United States Patent
Kim et al.

(10) Patent No.: US 7,229,827 B2
(45) Date of Patent: Jun. 12, 2007

(54) METHOD FOR DIFFERENTIATING MESENCHYMAL STEM CELLS INTO NEURAL CELLS

(75) Inventors: Hyun-Soo Kim, Suwon (KR); Hee-Hoon Yoon, Incheon (KR)

(73) Assignees: FCB-Pharmicell Co., Ltd. (KR); LifeCord International Co., Ltd. (KR)

( * ) Notice: Subject to any disclaimer, the term of this patent is extended or adjusted under 35 U.S.C. 154(b) by 637 days.

(21) Appl. No.: 10/475,056

(22) PCT Filed: Apr. 19, 2002

(86) PCT No.: PCT/KR02/00718

§ 371 (c)(1),
(2), (4) Date: Oct. 16, 2003

(87) PCT Pub. No.: WO02/086108

PCT Pub. Date: Oct. 31, 2002

(65) Prior Publication Data

US 2004/0151701 A1   Aug. 5, 2004

(30) Foreign Application Priority Data

Apr. 19, 2001   (KR) ............................ 2001-21064

(51) Int. Cl.
*C12N 5/00* (2006.01)
*C12N 5/06* (2006.01)
*C12N 5/08* (2006.01)

(52) U.S. Cl. ............... 435/377; 435/325; 435/372; 435/405

(58) Field of Classification Search ............... None
See application file for complete search history.

(56) References Cited

U.S. PATENT DOCUMENTS 5,753,506 A * 5/1998 Johe ........................ 435/377

OTHER PUBLICATIONS

Lindvall et al., Nature Medicine 10, S42-S50 (2004).*

* cited by examiner

*Primary Examiner*—David S Romeo
*Assistant Examiner*—Daniel C Gamett
(74) *Attorney, Agent, or Firm*—Anderson Kill & Olick, P.C.

(57) ABSTRACT

A method for differentiating mesenchymal stem cells of bone marrow into neural cells comprises culturing the mesenchymal stem cells in a medium containing epidermal growth factor(EGF), basic fibroblast growth factor(bFGF) and hepatocyte growth factor(HGF), and the neural cells produced thereby can be employed for the treatment of a neural disease.

7 Claims, 8 Drawing Sheets

METHOD FOR DIFFERENTIATING MESENCHYMAL STEM CELLS INTO NEURAL CELLS

FIELD OF THE INVENTION

The present invention relates to a method for differentiating mesenchymal stem cells in bone marrow into neural cells by culturing them in a medium containing epidermal growth factor(EGF), basic fibroblast growth factor(bFGF) and hepatocyte growth factor(HGF), and a composition for treating a neural disease comprising the neural cells as an active ingredient.

BACKGROUND OF THE INVENTION

Stem cells have the ability to divide indefinitely in culture and give rise to specialized cells constituting a tissue upon stimulation by a specific differentiation stimulus.

Stem cells are divided into embryonic stem cells(ES cells) and tissue-specific stem cells depending on their differentiation potencies. ES cells are isolated from the inner cell mass(ICM) of embryos at the blastocyst stage and are pluripotent, i.e., they are capable of differentiating into virtually every type of cells found in an organism.

In contrast, tissue-specific stem cells appear at a stage of organ formation during the embryonic development and they are organ-specific and multipotent, i.e., they are generally committed to give rise to cells constituting a specific organ. These tissue-specific stem cells remain in most of adult organs and perform the critical role of continually replenishing the loss of cells occurring normally or pathologically. Representative tissue-specific stem cells include hematopoietic stem cells and mesenchymal stem cells present in bone marrow. Hematopoietic stem cells give rise to various blood cells such as erythrocytes and leukocytes; and mesenchymal stem cells, to the cells of connective tissues, e.g., osteoblasts, chondroblasts, adipocytes and myoblasts.

Recently, clinical applications of the stem cells have drawn an increasing interest since the successful isolation of human embryonic stem cell. The most noticeable potential application of the stem cells is their use as a perfect source of cell supply for a cell replacement therapy. Hardly curable diseases, e.g., neurodegenerative disease such as Parkinson's and Alzheimer's diseases, quadriplegia resulting from spinal cord injury, leukemia, apoplexy, juvenile-onset diabetes, cardiac infarction and liver cirrhosis, are caused by the disruption and permanent functional disorder of the cells constituting an organ, and the cell replacement therapy, wherein the loss of cells is replenished from the outside, has been presented as an effective remedy.

However, notwithstanding the obvious benefit of the cell replacement therapy, there exist many limitations in its clinical applications. Specifically, the conventional method, wherein fully differentiated cells isolated from the tissues of a donor are transplanted into a patient, has the problem that it is difficult to obtain a sufficient amount of cells to be supplied to the patient. In order to solve this problem, cells of a specific tissue differentiated from an isolated embryonic stem cell or differentiated cells from isolated and proliferated tissue-specific stem cells can be employed in a cell replacement therapy.

Hitherto, it has been proven that mouse embryonic stem cells can be differentiated on a culture dish into various cells such as hematopoietic cells, myocardial cells, insulin-secreting pancreatic cells and neural cells. Further, several reports have demonstrated that transplantation of the cells differentiated from stem cells is effective in the treatment of a disease caused by the loss of cells. For instance, synthesis of myelin in a mouse increased when myelin-synthesizing oligodendrocytes differentiated from an embryonic stem cell were transplanted into the mouse(Brustle et al., *Science*, 285: 754–756, 1999). Blood sugar level was regulated by transplanting insulin-secreting cells differentiated from an embryonic stem cell into a diabetes mouse model (Soria et al., *Diabetes*, 49: 157–162, 2000). Further, dyscinesia caused by spinal cord injury was remedied significantly by transplanting neural cells differentiated from an embryonic stem cell into a mouse having spinal cord injury(McDonald et al., *Nat. Med.*, 5(12): 1410–1412, 1999).

However, since the human embryonic stem cell has been successfully isolated only recently and there is no report on the differentiation of the embryonic stem cell on a culture dish into other specific cells than neural cells, clinical use of specific tissue cells differentiated from an embryonic stem cell in a cell replacement therapy still remains on a level of possibility.

Further, since the efficiency of differentiation from an embryonic stem cell into target cells is low, there is a risk of an adverse side effect caused by other cells mixed with the target cells during transplantation. Accordingly, there exists a need for the development of a precise differentiation method for safer clinical application of the cells differentiated from embryonic stem cells.

On the other hand, in case when tissue-specific stem cells are employed in a cell replacement therapy, there is the problem that lowering of the proliferating ability of the cells or differentiation into unfavorable cells may occur during a long-term culture. Further, transplantation of neural cells is required for the treatment of a neurodegenerative disease such as Parkinson's disease. Since it is difficult to obtain neural stem cells directly from the patient, they are generally obtained by culturing neural stem cells isolated from the brain tissue of dead fetus and differentiating them into neural cells. However, the use of fetal brain invites the ethical problem as well as is limited by insufficient supply, and may cause an immunological rejection. Further, most of neural stem cells are liable to differentiate into astrocytes rather than neurons.

Accordingly, if it is possible to differentiate mesenchymal stem cells in patient's own bone marrow into neural cells to be used in a cell replacement therapy, neural cells can be readily supplied and such problems as immunological rejection would not occur during treatment.

Hitherto, it has been considered that one kind of stem cells differentiate only into the cells of a tissue belonging to a specific system. It was reported that mesenchymal stem cells formed in vitro colonies in the presence of various growth factors such as platelet-derived growth factor, basic fibroblast growth factor(bFGF), transforming growth factor-$\beta$ (TGF-$\beta$) and epidermal growth factor(EGF)(Kuznetsov et al., *Br. J. Haematol.*, 97: 561, 1997; and van den Bos C. et al., *Human Cell*, 10:45, 1997), and about one-third of initially attached cells had a multipotency, thereby differentiating into connective tissue cells such as osteoblasts, chondroblasts and adipocytes(Pittenger M F et al., *Science*, 284: 143, 1999). Further, Ferrari G. et al. reported that bone marrow is a source of myogenic precursor cells that form new muscles(*Science*, 279: 1528, 1998).

Recent studies reported that mesenchymal stem cells can also differentiate into the cells of the neural system. For instance, Sanchez-Ramos et al. reported that mesenchymal stem cells differentiated into neurons and astrocytes upon culture in the presence of retinoic acid and brain-derived neurotrophic factor(BDNF)(*Exp. Neurology*, 164: 247–256, 2000). Dale Woodbury et al. reported that mesenchymal stem cells in bone marrow differentiated into neural cells in the presence of antioxidants such as β-mercaptoethanol and dimethyl sulfoxide(DMSO)(*J. Neuro. Res.*, 61: 364–370, 2000). However, the use of strong differentiation-inducing agents such as DMSO may cause a problem in a clinical application.

The present inventors have endeavored to discover materials that are highly safe and capable of differentiating stem cells in bone marrow into neural cells, and have discovered that HGF promotes the differentiation of mesenchymal stem cells of bone marrow into neural cells, and also that the addition of EGF and bFGF to a culture medium, together with HGF, significantly enhances both the differentiation of stem cells into neural cells and the amplification of the resulting neural cells.

It has been reported that EGF and bFGF stimulate the differentiation of neural stem cells into neurons or astrocytes when they are added to a serum-free medium for culturing neural stem cells separated from the brain tissue (Melissa et al., *Exp. Neurology*, 158: 265–278, 1999).

HGF has been reported to enhance the viability of neurons in hippocampus and mesencephalon, and induce the growth of neurite in neocortical explant(Hamanoue M et al., *J. Neurosci. Res.*, 43: 554–564, 1996). Further, in the peripheral nervous system, it functions as an existence factor for motoneurons(Ebens A et al., *Neuron*, 17: 1157–1172, 1996), and involves in the growth and existence of sensory neurons and parasympathetic neurons (Fleur Davey et al., *Mol. Cell Neurosci.*, 15: 79–87, 2000).

However, it has never been reported that mesenchymal stem cells can be differentiated into neural cells by culturing them in a medium containing EGF, bFGF and HGF.

SUMMARY OF THE INVENTION

Accordingly, it is an object of the present invention to provide a method for differentiating mesenchymal stem cells or mononuclear cells in bone marrow into neural cells.

It is another object of the present invention to provide neural cells differentiated by said method and a pharmaceutical composition for treating a neural disease comprising the neural cells as an active ingredient.

It is a further object of the present invention to provide a method for treating a neural disease in a mammal, which comprises administering the neural cells produced by the above method to a subject in need thereof.

In accordance with one aspect of the present invention, therefore, there is provided a method for differentiating mesenchymal stem cells in bone marrow into neural cells, which comprises culturing the mesenchymal stem cells in a medium containing epidermal growth factor(EGF), basic fibroblast growth factor(bFGF) and hepatocyte growth factor(HGF).

BRIEF DESCRIPTION OF THE DRAWINGS

The above and other objects and features of the present invention will become apparent from the following description of the invention, when taken in conjunction with the accompanying drawings, which respectively show:

FIGS. 4A to 4C: the results of immunocytochemical staining of differentiated neural cells of FIG. 2, wherein FIG. 4A is NSE-positive cells; FIG. 4B, NeuN-positive cells and FIG. 4C, GFAP-positive cells;

FIGS. 8A to 8C: the results of immunocytochemical staining of the differentiated neural cells of FIG. 7, wherein FIG. 8A is NSE-positive cells; FIG. 8B, NeuN-positive cells and FIG. 8C, GFAP-positive cells.

DETAILED DESCRIPTION OF THE INVENTION

The present invention provides a method for differentiating mesenchymal stem cells isolated from bone marrow into neural cells, which comprises culturing the mesenchymal stem cells in a medium containing epidermal growth factor (EGF), basic fibroblast growth factor (bFGF) and hepatocyte growth factor (HGF).

Further, neural cells differentiated by said method and a pharmaceutical composition for treating a neural disease comprising the neural cells as an active ingredient are also provided.

As used herein, the term "neural cells" refers to the nerve-like cells including neurons, astrocytes and microglias.

In order to differentiate mesenchymal stem cells into neural cells, it is preferred to culture the mesenchymal stem cells in a cell culture medium containing 1 to 1,000 ng/ml, preferably, 5 to 10 ng/ml of EGF, 1 to 1000 ng/ml, preferably, 10 to 20 ng/ml of bFGF and 1 to 1000 ng/ml, preferably, 5 to 20 ng/ml of HGF for more than one week. It is more preferable to culture the stem cells for more than 4 weeks. About 4 weeks after the initiation of culture, neural cell colonies consisting of several cells are formed and, after about 8 weeks, a massive amount of neural cells are produced by the continuous growth and proliferation of the neural cell colonies.

In contrast, if the mesenchymal stem cells are cultured in the same medium but lacking HGF, the cells can not differentiate into neural cells. Further, if they are treated with HGF only, early differentiation occurs, thereby preventing proliferation. This result suggests that, in the inventive process of culturing mesenchymal stem cells to obtain neural cells, EGF and bFGF stimulate the cells to proliferate and HGF stimulates the stem cells to differentiate into neural cells. Further, a sufficient amount of neural cells cannot be obtained when only one of the factors is employed.

Once the neural cells are completely differentiated and proliferated after 8-week culture, they can further proliferate without losing their unique characteristics as neural cells even when treated only with EGF and bFGF. On the other hand, if the fully differentiated and proliferated neural cells are subsequently treated with HGF only, the cells differentiate continuously without proliferation and, consequently, the number of cells decreases. Accordingly, after culturing for 8 weeks, it is preferred to allow the neural cells to proliferate by further culturing them in a medium containing EGF and bFGF.

According to the present method using EGF, bFGF and HGF, more than 80% of the total differentiated cells are neural cells, which comprises 60 to 80%, preferably 65 to 75%, of neurons and 20 to 40%, preferably 25 to 35%, of astrocytes, based on the number of cells, and contains no microglia.

In the present invention, mesenchymal stem cells are preferably obtained from human bone marrow. Mononuclear cells derived from bone marrow contains hematopoietic and mesenchymal stem cells, and when they are cultured for 1 to 2 weeks, hematopoietic stem cells easily differentiate into mature blood cells. Accordingly, the stem cells proliferating thereafter are mesenchymal stem cells, which continue to prolifereate after 20 passages of subculture. The mesenchymal stem cells differentiate into various connective tissue cells including osteoblasts, chondroblasts and adipocytes.

In addition, massive production of neural cells can also be achieved when the mononuclear cells of bone marrow including the mesenchymal stem cells are used in the method of the present invention, in place of the isolated mesenchymal stem cells.

The present method is advantageous especially in terms of safety, since the neural cells are differentiated from the mesenchymal stem cells by employing as inducers the specific proteins present in a human body, i.e., EGF, bFGF and HGF, without using a harmful differentiation inducer such as DMSO. Further, since a sufficient amount of neural cells necessary for the treatment of a disease can be produced from patient's own bone marrow, a clinical application thereof would be viable owing to ready availability of neural cells and reduced risk of immunological rejections.

The neural cells differentiated from mesenchymal stem cells in accordance with the present invention can be used as an active ingredient of a cell composition for a cell replacement therapy for a neural disease. Non-limiting examples of neural diseases, which can be treated by using the neural cells of the present invention, include neurodegenerative diseases such as Parkinson's disease, Alzheimer's disease, Pick's disease, Huntington's disease, amyotrophic lateral sclerosis and ischemic brain disease. The inventive neural cells can also be used in the treatment of various diseases caused by unusual loss of neural cells as well as dyscinesia caused by a spinal cord injury.

A cell composition for preventing or treating neural diseases can be prepared by mixing the neural cells differentiated by the inventive method with a pharmaceutically acceptable excipient or carrier, or by diluting it with a pharmaceutically acceptable diluent in accordance with any of the conventional procedures. Examples of suitable carriers, excipients, and diluents are lactose, dextrose, sucrose, sorbitol, mannitol, xylitol, erythritol, maltitol, starches, gum acacia, alginates, gelatin, calcium phosphate, calcium silicate, cellulose, methylcellulose, microcrystalline cellulose, polyvinylpyrrolidone, water, methylhydroxybenzoates, propylhydroxy-benzoates, talc, magnesium stearate and mineral oil. The formulations may additionally include fillers, antiagglutinating agents, lubricating agents, wetting agents, flavors, emulsifiers, preservatives and the like. The cell composition of the present invention may be formulated so as to provide quick, sustained or delayed release of the active ingredient after their administration to a mammal by employing any of the procedures well known in the art. Thus, the formulations may be in the form of a sterile injectable solution, suspension, emulsion, solution and the like, wherein a sterile injectable solution is preferred.

Accordingly, the present invention also provides a method for treating a neural disease in a mammal, which comprises administering the neural cells produced by the inventive method to a subject in need thereof in an amount effective for treating the disease.

The neural cells produced by the inventive method may be injected into the body of a patient by any of the conventional methods. For instance, the method of Douglas Kondziolka(D. Kondziolka et al., *Neurology* 55: 556–569, 2000) may be used. Specifically, the cranium of the patient is excised to create an opening having a diameter of about 1 cm, and a HBSS (Hank's balanced salt solution) containing neural cells is injected in about three spots. The injection is carried out by a syringe having a long needle and a stereotactic frame for injecting the desired cell solution into a deep part of the brain at a correct position. The cell composition of the present invention can be administered via various routes including transdermal, subcutaneous, intravenous and intramuscular introduction, surgical stereotactic introduction, intralesional introduction by vascular catheterization.

Typical unit dose of the neural cells may range from $1 \times 10^6$ to $1 \times 10^9$ cells and they can be administered every week or every month. However, it should be understood that the amount of the active ingredient actually administered ought to be determined in light of various relevant factors including the disease to be treated, the severity of the patient's symptom, the chosen route of administration, and the age, sex and body weight of the individual patient; and, therefore, the above dose should not be intended to limit the scope of the invention in any way.

The following Examples are intended to further illustrate the present invention without limiting its scope.

Further, percentages given below for solid in solid mixture, liquid in liquid, and solid in liquid are on a wt/wt, vol/vol and wt/vol basis, respectively, and all the reactions were carried out at room temperature, unless specifically indicated otherwise.

EXAMPLE 1

Isolation of Mononuclear Cells in Bone Marrow

About 10 ml of bone marrow was taken from the pelvis of each of healthy volunteers and stored in glass tubes containing heparin. 30 ml of phosphate buffered saline(PBS) was added to 10 ml of bone marrow, and 20 ml of the resulting mixture was slowly transferred onto 10 ml of Ficoll-Paque™ plus solution(1.077 g/ml, Amersham Pharmacia Biotech), and subjected to density gradient centrifugation at 2000 rpm for 20 minutes. The mononuclear cell layer at the interface between the top layer and Ficoll-Paque™ plus layer was recovered and subject to centrifugation at 1800 rpm for 5 minutes to obtain mononuclear cells.

EXAMPLE 2

Culture of Mononuclear Cells

The mononuclear cells obtained in Example 1 were inoculated at a density of $1 \times 10^6$ cells/cm$^2$ to a culture flask containing a basal medium. The flask was incubated at 37° C., 5% $CO_2$. After 4 hours, the flask was washed with fresh basal medium to remove non-attached cells. The basal medium was Williams' E medium(Gibco BRL) containing 3.5 μM of hydrocortisone(Sigma), 50 ng/ml of linoleic acid(Sigma Co.) mixed with fatty acid-free bovine serum albumin(Gibco BRL) at an equal molar ratio, 0.1 μM $CuSO_4.5H_2O$ (Sigma), 50 pM $ZnSO_4.7H_2O$ (Sigma), 3 ng/ml $H_2SeO_3$ (Sigma), 1.05 mg/ml $NaHCO_3$(Sigma Co.), 1.19 mg/ml HEPES(Sigma), 100 U/ml penicillin(Gibco BRL), 10 mg/ml streptomycin(Gibco BRL) and 25 μg/ml amphotericin(Gibco BRL).

EXAMPLE 3

Differentiation of Mononuclear Cells into Neural Cells

In order to confirm whether the mononuclear cells obtained in Example 2 differentiate into neural cells, the mononuclear cells were cultured at 37° C., 5% $CO_2$ on a basal medium containing 10 ng/ml of epidermal growth factor(Gibco BRL), 20 ng/ml of basic fibroblast growth factor(R&D Systems) and 20 ng/ml of hepatocyte growth factor(R&D Systems) ("differentiating medium"). The differentiating medium was replenished two times a week.

Figure 1:
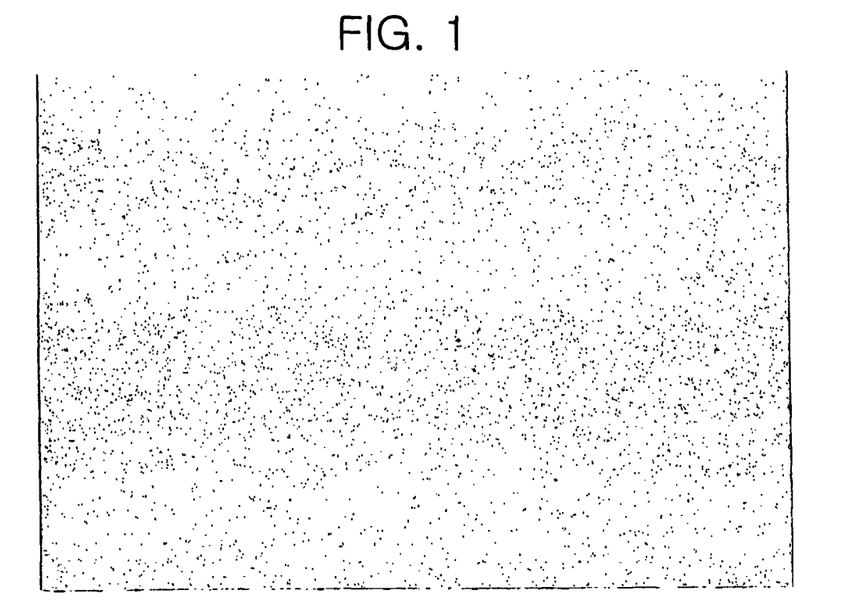
FIG. 1: a photomicrograph(×100; hereinafter, same magnification is applied) of the attached cells derived from mononuclear cells of bone marrow cultured for 4 weeks on a medium containing 10 ng/ml EGF, 20 ng/ml bFGF and 20 ng/ml HGF.

About 4 weeks after, neural cell colonies appeared and continuously proliferated(see Table 1 and FIG. 1).

Figure 2:
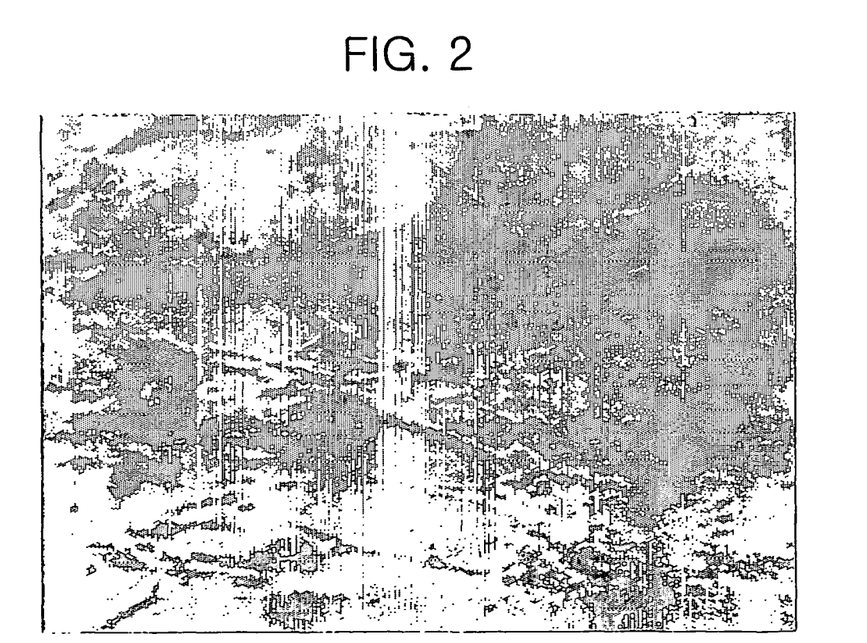
FIG. 2: a photomicrograph of the neural cells differentiated from mononuclear cells of bone marrow cultured for 8 weeks on a medium containing 10 ng/ml EGF, 20 ng/ml bFGF and 20 ng/ml HGF.
Figure 3A:
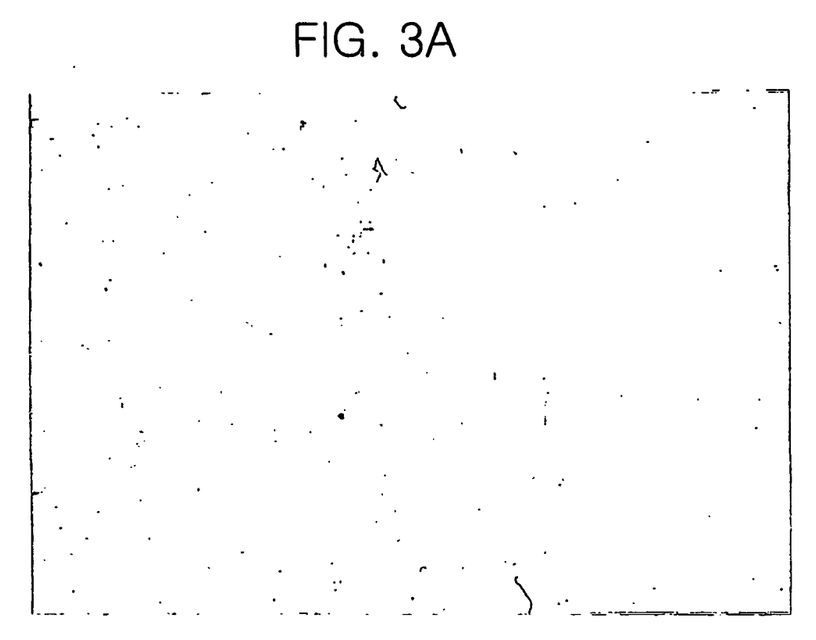
FIGS. 3A and 3B: photomicrographs of a neuron and an astrocyte, respectively, which are isolated from the neural cells of FIG. 2.
Figure 3B:
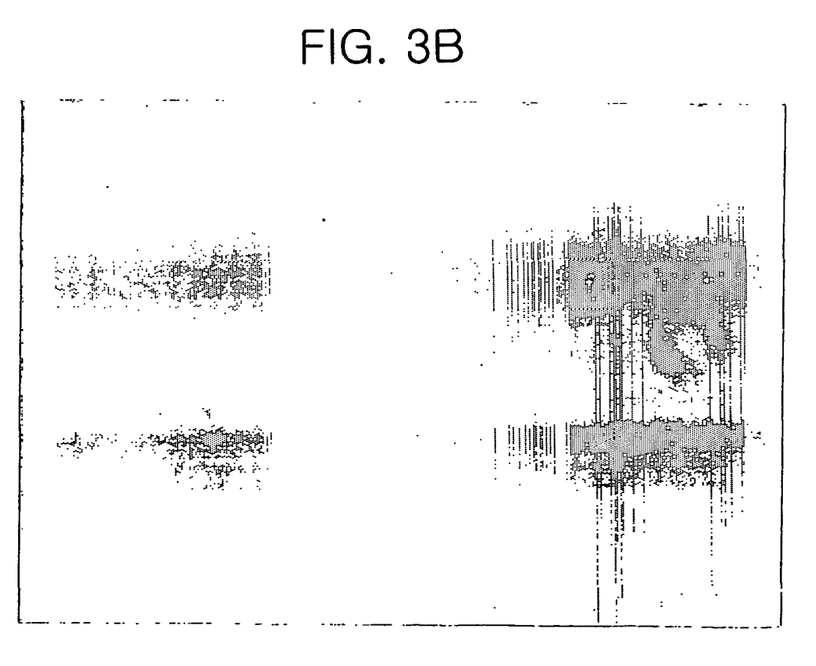

About 8 weeks after, neuron-form cells consisting of long projections such as axons and short projections such as dendrites, and astrocyte-form cells consisting only with short dendrites were observed (see FIGS. 2 and 3). Further, after 8 weeks, the cells proliferated with their shapes unaltered, even if cultured on a basal medium containing only EGF and bFGF(see Table 2).

However, when the mesenchymal stem cells were cultured in a medium containing only EGF and bFGF, the cells did not differentiate into neural cells. Further, when the mesenchymal stem cells were cultured in a medium containing HGF only, the cells differentiated early and, accordingly, they neither grew nor proliferated(see Table 1).

TABLE 1

Number of cells/ml of culture after 8-week culture of mesenchymal stem cells

| No. of inoculated cells | No growth factor | Treatment with HGF | Treatment with EGF and bFGF | Treatment with EGF, bFGF and HGF |
| --- | --- | --- | --- | --- |
| $7.5 \times 10^7$ | Not proliferated | Not proliferated | $1 \times 10^5$ | $2 \times 10^5$ |

TABLE 2

Proliferation of cells after 4- or 8-week culture of neural cells differentiated from mesenchymal stem cells by 8-week culture on a medium containing EGF, bFGF and HGF (No. of inoculated cells: $1 \times 10^5$)

| | No growth factor | Treatment with HGF | Treatment with EGF and bFGF | Treatment with EGF, bFGF and HGF |
| --- | --- | --- | --- | --- |
| After 4 weeks | Not proliferated | Not proliferated | $2 \times 10^5$ | $2 \times 10^5$ |
| After 8 weeks | Not proliferated | Not proliferated | $5 \times 10^5$ | $1 \times 10^5$ |

EXAMPLE 4

Immunocytochemistry

The neural cells obtained in Example 3, which were differentiated from the mononuclear cells of bone marrow by culturing on a medium containing EGF, bFGF and HGF for 8 weeks, were attached on a 1 cm$^2$ cover glass at a density of $1 \times 10^4$ cells/cm$^2$. The cells were washed with 0.1 M phosphate buffer for 5 minutes, fixed with 0.1 M phosphate buffer containing 4% paraformaldehyde for 15 minutes, and washed twice with 0.1 M phosphate buffered saline(PBS). The cells were treated with 0.1 M PBS containing 1% BSA and 0.2% Triton X-100 for 5 minutes, and then, reacted for 16 hours with first antibodies; mouse anti-human neuron-specific enolase(NSE)(Chemicon Inc.), mouse anti-human neuron-specific nuclear protein (NeuN) (Chemicon Inc.), mouse anti-human β-tubulin III (Sigma Co.) and mouse anti-human glial fibrillary acidic protein (GFAP)(Sigma Co.).

Upon completion of the reaction with the first antibodies, the remaining antibodies were removed and the cells were washed twice with 0.1 M PBS containing 0.5% BSA each for 15 minutes. A secondary antibody, rabbit anti-mouse IgG (Sigma Co.) was added thereto and incubated for 30 minutes. The cells were washed with 0.1 M PBS containing 0.5% BSA each for 5 minutes. The reaction was carried out for 30 minutes by employing Vectastain Elite ABC kit (Vector Laboratory Inc.) containing avidin-biotin. The cells were washed twice with 0.1 M phosphate buffer each for 5 minutes, DAB (3,3'-diaminobenzidine tetrahydrochloride dehydrate, Sigma Co.) was added thereto as a color developing substrate, and the mixture was allowed to react for 5 minutes. The reaction was stopped by treating the reactants with 0.1 M phosphate buffer for 5 minutes and washing them twice with the buffer each for 5 minutes. The resulting reactants were dried and washed with distilled water for 5 minutes. The cells were dehydrated and fixed by treating sequentially with distilled water, and 70%, 80%, 95% and 100% ethanol.

Figure 4A:
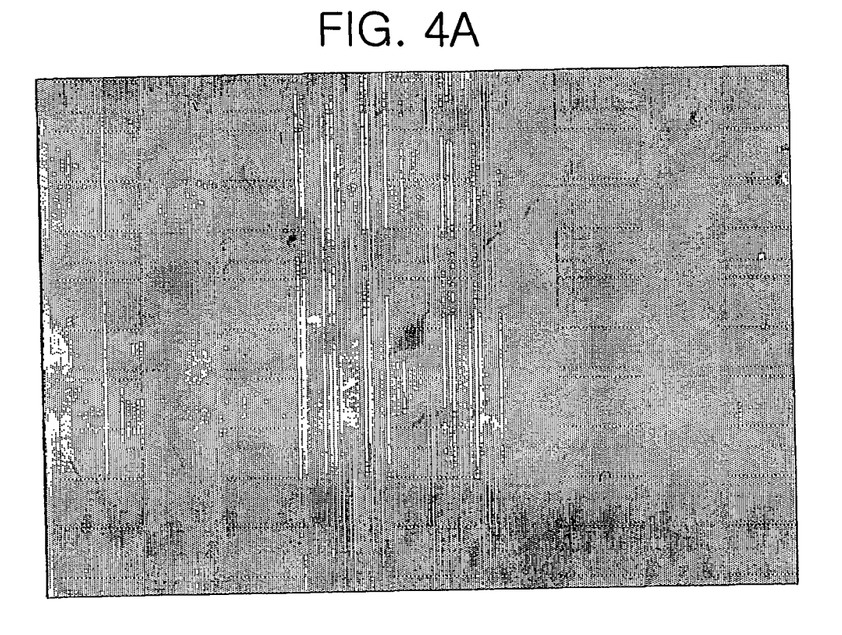
Figure 4B:
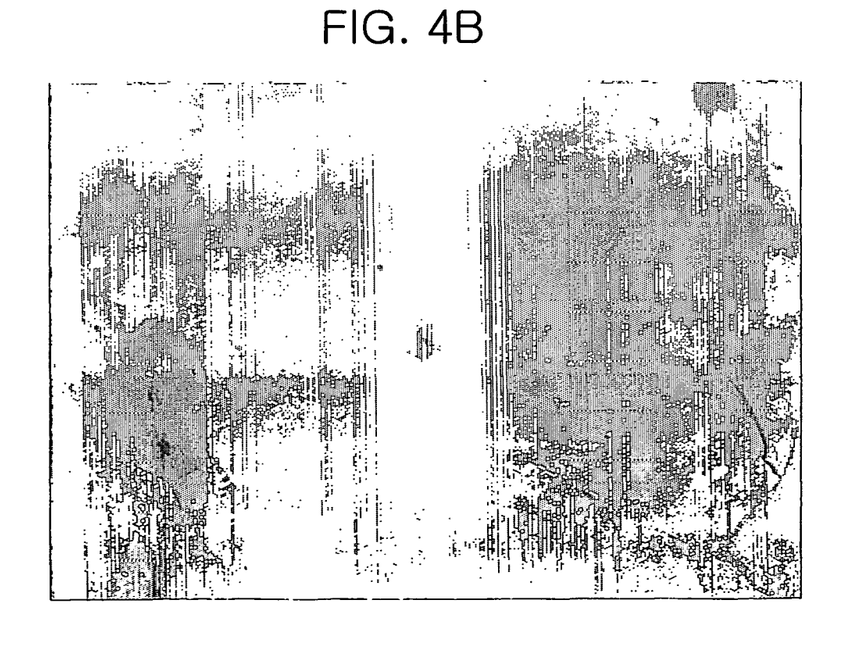
Figure 4C:
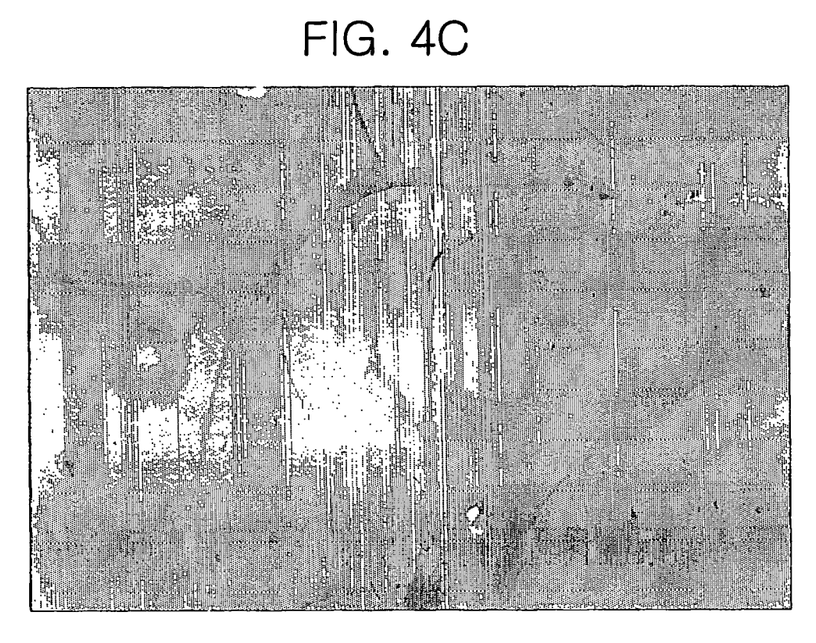

The results of the above immunocytochemical staining are shown in FIGS. 4A to 4C, wherein the differentiated cells exhibit positive results for neuronal markers NeuN, NSE and β-tubulin III, and astroglial marker GFAP. These results show that the cells were differentiated into neurons and astrocytes, as judged by their biochemical as well as morphological characteristics. However, the cells were negative for microglial marker OX-42, demonstrating that the mononuclear cells did not differentiate into microglia.

The proportions of neurons(which is positive for NeuN and NSE) and astrocytes(which is positive for GFAP) in the cells differentiated from the mononuclear cells of bone marrow by culturing on a medium containing EGF+bFGF+HGF or EGF+bFGF for 8 weeks, were examined and shown in Table 3.

TABLE 3

|  | NSE | NeuN | GFAP | Negative cells |
|---|---|---|---|---|
| EGF + bFGF | ab. 0.9% | Ab. 0.8% | ab. 1.2% | ab. 89% |
| EGF + bFGF + HGF | ab. 56% | Ab. 75% | ab. 24% | ab. 20% |

As can be seen from Table 3, about 80% of the total differentiated cells are neural cells when cultured on a medium containing EGF+bFGF+HGF for 8 weeks. The neural cells consisted of about 70% neurons and about 30% astrocytes.

EXAMPLE 5

Isolation and Culture of Mesenchymal Stem Cell

In order to see whether the mesenchymal stem cells in the mononuclear cells of bone marrow would differentiate into neural cells, the mononuclear cells were cultured and mesenchymal stem cells were isolated therefrom. The mesenchymal stem cells were examined for their capability to differentiate into various cells, as follows.

The mononuclear cells cultured as in Example 2 were inoculated in a culture flask containing DMEM (Gibco BRL) supplemented with 10% FBS (fetal bovine serum), at a density of $1 \times 10^3$ cells/cm$^2$. The cells were cultured at 37° C. under an atmosphere of 5% $CO_2$. After 1~2 weeks, the proliferated cells were subjected to a subculture, and the proliferation continued after 20 passages of subculture.

Mononuclear cells obtained from bone marrow include mature leukocytes, lymphocytes, scleroblasts, chondrocytes, muscle cells, fibroblasts, adipocytes as well as stem cells to be differentiated into these cells, said stem cells being divided into hematopoietic and mesenchymal stem cells. The hematopoietic stem cells, which give rise to blood cells such as erythrocytes, leukocytes and lymphocytes, can not proliferate but easily differentiate into mature blood cells in a general culture medium. Accordingly, it can be seen that the cells proliferating continuously as above are mesenchymal stem cells.

In order to confirm whether the proliferating cells are indeed mesenchymal stem cells, the cells were treated with various cytokines and chemical agents and their differentiation into various connective tissue cells, including osteoblasts, chondroblasts and adipocytes, was examined in accordance with the method of Pittenger et al., *Science*, 284: 143–147, 1999.

In order to differentiate the stem cells into osteoblasts, the cells were treated with 100 mM dexamethasone, 10 mM β-glycerol phosphate and 50 nM ascorbate-2-phosphate and 10% FBS.

Further, in order to confirm the capability of the stem cells to differentiate into chondroblasts, cultured stem cells were centrifuged to obtain cell pellets, which were treated with 100 nM dexamethasone and 10 ng/ml TGF-β 3 in the absence of serum.

The differentiation of the stem cells into adipocytes was induced by treating the stem cells with 0.5 mM 1-methyl-3-isobutylxanthine, 1 mM Dexamethasone, 10 g/ml insulin, 100 nM indomethacine and 10% FBS.

Osteoblasts were examined by alkaline phosphatase staining(Jaiswal et al., *J. Cell Biochem.*, 64(2): 295–312, 1997); chondroblasts, by type II collagen RT-PCR(Mackay et al., *Tissue Eng.*, 4(4): 415–428, 1998) and staining with toluidine blue; adipocytes, by staining with oil red O.

Figure 5A:
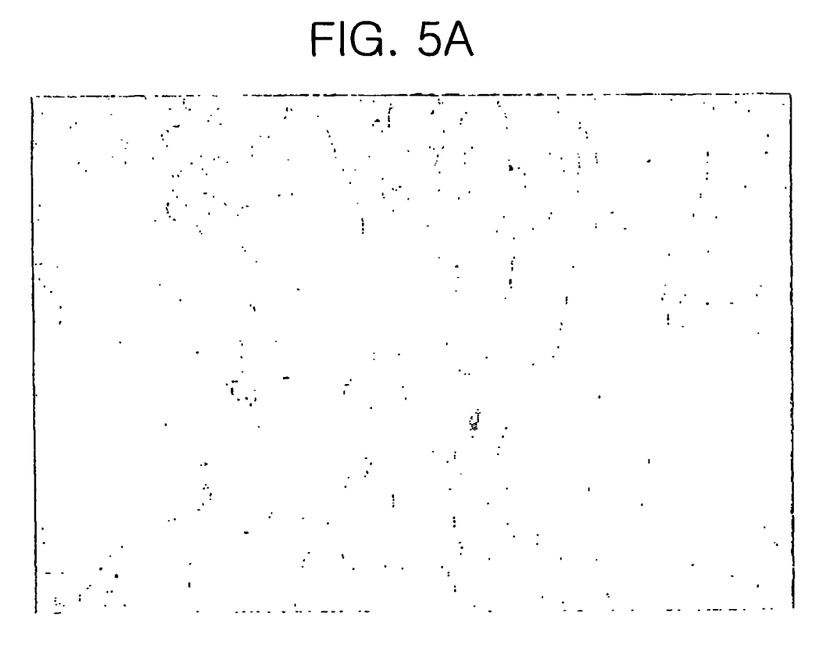
FIGS. 5A to 5C: photomicrographs of osteoblasts, chondroblasts and adipocytes, respectively, differentiated from mesenchymal stem cells.
Figure 5B:
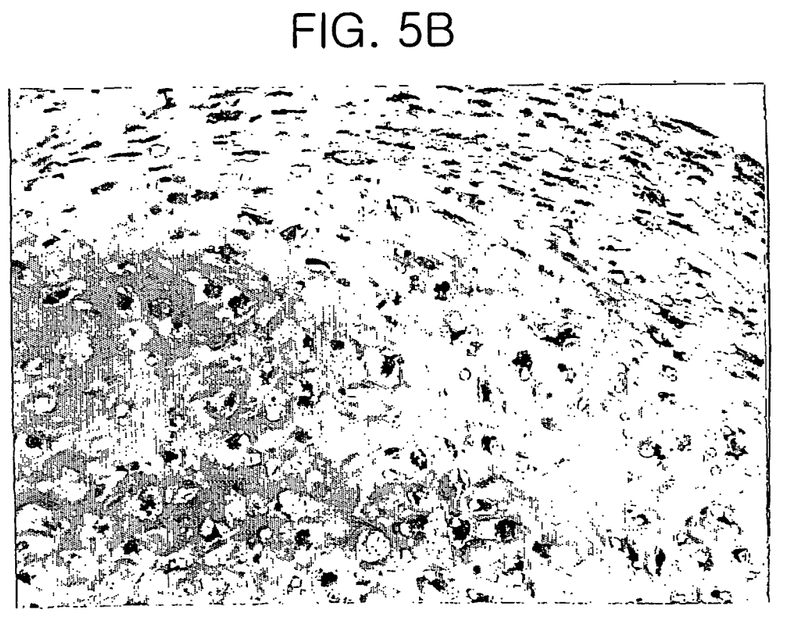
Figure 5C:
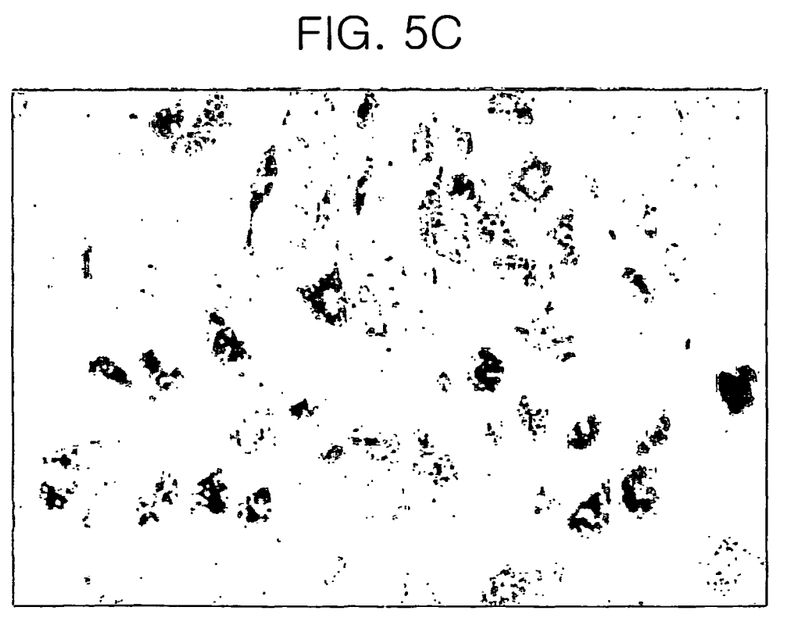

Consequently, as can be seen from FIGS. 5A, 5B and 5C, positive results were observed under a light microscope in all of the samples. These results demonstrate that the mesenchymal stem cells cultured and proliferated in vitro still maintain the properties of stem cells capable of differentiating into various connective tissue cells such as osteoblasts, chondroblasts and adipocytes.

EXAMPLE 6

Differentiation of Mesenchymal Stem Cells into Neural Cells

To examine whether the mesenchymal stem cells isolated in Example 5 can differentiate into neural cells, the mesenchymal stem cells were cultured for 8 weeks in a medium supplemented with EGF, bFGF and HGF, according to the procedure of Example 3.

Figure 6:
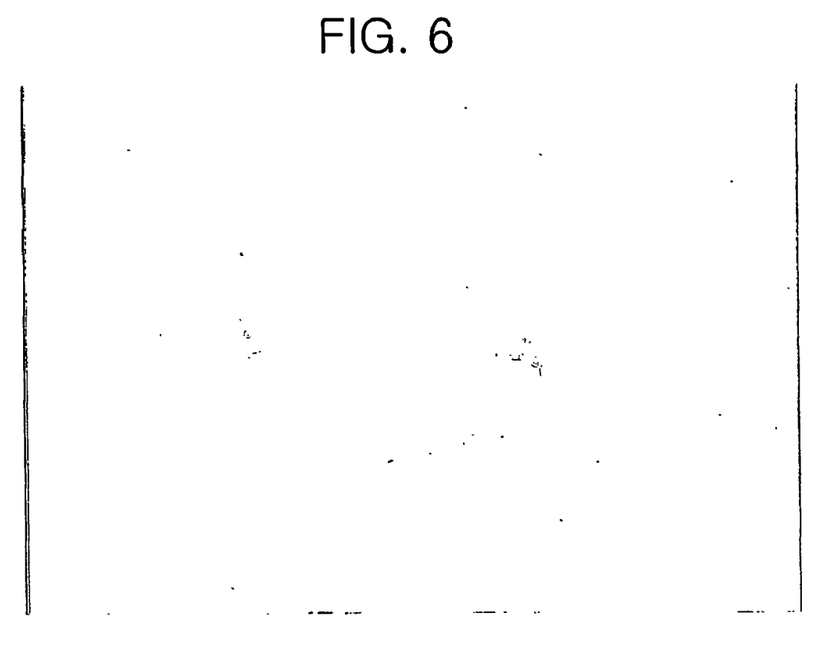
FIG. 6: a photomicrograph of mesenchymal stem cells taken immediately after its inoculation on a medium containing 10 ng/ml EGF, 20 ng/ml bFGF and 20 ng/ml HGF.
Figure 7:
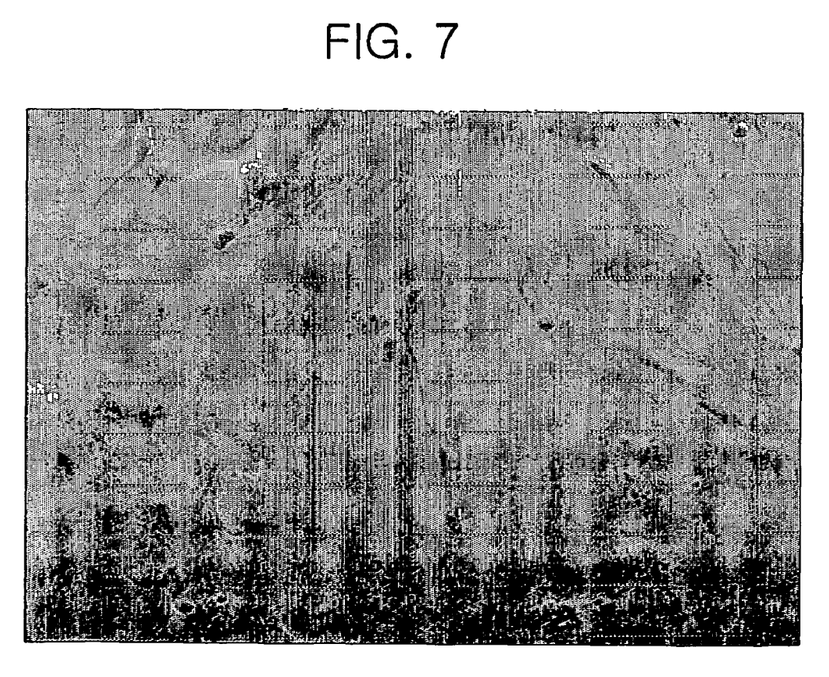
FIG. 7: a photomicrograph of neural cells differentiated from the mesenchymal stem cells cultured for 8 weeks on a medium containing 10 ng/ml EGF, 20 ng/ml bFGF and 20 ng/ml HGF.

Consequently, like the differentiation of neural cells from mononuclear cells in bone marrow, neural cell colonies were formed after 4 weeks and the neural cells grew and proliferated continuously until the 8th week. FIGS. 6 and 7 illustrate photomicrographs of the cells taken immediately after inoculation and after 8-week culture, respectively.

After 8th week, the cells continuously proliferated while maintaining the morphological characteristics of neural cells even when they were treated only with EGF and bFGF.

Also, immunocytochemical staining was carried out with the differentiated cells, according the procedure of Example 4.

Figure 8A:
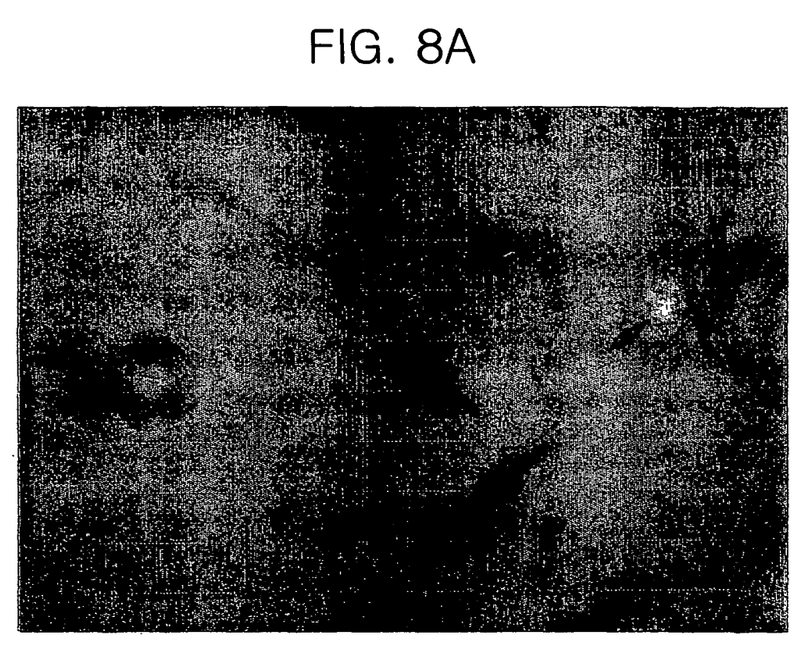
Figure 8B:
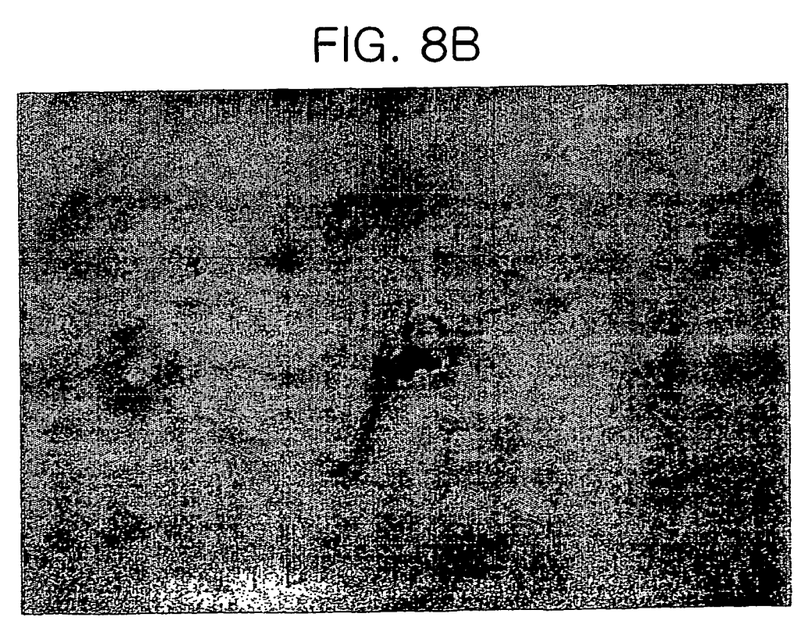
Figure 8C:
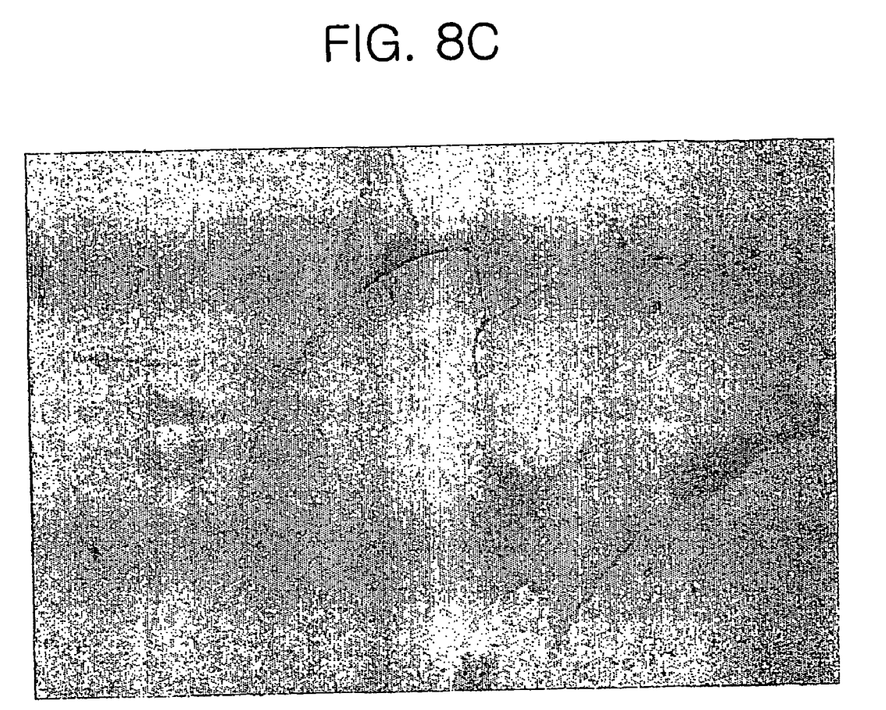

Consequently, like the results obtained for the neural cells derived from mononuclear cells of bone marrow, the differentiated cells were tested positive for neural markers NeuN, NSE and β-tubulin III and astroglial marker GFAP. Accordingly, it was confirmed that mesenchymal stem cells differentiate into both neurons and astrocytes(see FIGS. 8A to 8C). FIGS. 8A to 8C show the results of immunocytochemical staining, FIG. 8A representing NSE-positive cells; FIG. 8B, NeuN-positive cells; and FIG. 8C, GFAP-positive cells.

While the invention has been described with respect to the above specific embodiments, it should be recognized that various modifications and changes may be made to the invention by those skilled in the art which also fall within the scope of the invention as defined by the appended claims.

What is claimed is:

1. A method for differentiating mesenchymal stem cells into neural cells, which comprises culturing the mesenchymal stem cells in a medium containing epidermal growth factor (EGF), basic fibroblast growth factor (bFGF) and hepatocyte growth factor (HGF).

2. The method of claim 1, wherein the mesenchymal stem cells are cultured in a medium containing 1 to 1000 ng/ml of EGF, 1 to 1000 ng/ml of bFGF and 1 to 1000 ng/ml of HGF for more than one week.

3. The method of claim 2, wherein the culturing is carried out for more than 4 weeks.

4. The method of claim 1, wherein the mesenchymal stem cells are cultured in a medium containing EGF, bFGF and HGF for more than one week and the resulting differentiated neural cells are allowed to proliferate in a medium containing EGF and bFGF.

5. The method of claim 1, wherein the mesenchymal stem cells are isolated from human bone marrow.

6. The method of claim 1, wherein mononuclear cells isolated from bone marrow and containing mesenchymal stem cells are used as a source of mesenchymal stem cells.

7. The method of claim 1, wherein the neural cells contain neurons and astrocytes.

* * * * *